United States Patent [19]
Thompson

[11] Patent Number: 5,674,375
[45] Date of Patent: Oct. 7, 1997

[54] METHOD FOR DETECTING THE PRESENCE OR ABSENCE OF CORROSION OF CATHODICALLY PROTECTED STRUCTURES

[75] Inventor: Neil G. Thompson, Dublin, Ohio

[73] Assignee: Gas Research Institute, Chicago, Ill.

[21] Appl. No.: 766,966

[22] Filed: Sep. 26, 1991

Related U.S. Application Data

[63] Continuation of Ser. No. 164,930, Mar. 7, 1988, abandoned.

[51] Int. Cl.$^6$ ................................................ G01N 27/02
[52] U.S. Cl. .......................... 205/734; 204/196; 205/724; 324/700
[58] Field of Search .......................... 204/153.11, 147, 204/196, 404; 324/700; 205/724, 734, 725

[56] References Cited

U.S. PATENT DOCUMENTS

| | | | |
|---|---|---|---|
| 4,090,170 | 5/1978 | Lincklaen-Arriens et al. . | |
| 4,238,298 | 12/1980 | Tsuru et al. | 324/57 R X |
| 4,591,792 | 5/1986 | Birchmeier et al. . | |
| 4,658,363 | 4/1987 | Syrett et al. . | |
| 4,831,324 | 5/1989 | Asakura et al. | 204/404 X |

OTHER PUBLICATIONS

John et al., "Use of AC . . . Conditions", Br. Coros. J., 1981, vol. 16, No. 2, pp. 102–106.

Bard et al., "Electrochemical Methods", Chapter 9, pp. 316 to 367, Wiley & Sons, Inc.

*Primary Examiner*—Nam Nguyen
*Attorney, Agent, or Firm*—Speckman, Pauley & Fejer

[57] ABSTRACT

A method for detecting the presence or absence of corrosion of cathodically protected steel structures in soil and concrete in which the cathodic protection circuit is subjected to an electrochemical impedance spectroscopic analysis and the presence of corrosion is indicated by the presence of a Warburg impedance.

2 Claims, 5 Drawing Sheets

5,674,375

METHOD FOR DETECTING THE PRESENCE OR ABSENCE OF CORROSION OF CATHODICALLY PROTECTED STRUCTURES

This is a continuation of U.S. patent application Ser. No. 07/164,930 filed Mar. 7, 1988, abandoned.

FIELD OF THE INVENTION

This invention relates to a method for detecting the presence or absence of corrosion of cathodically protected steel structures in soil and concrete.

BACKGROUND AND SUMMARY OF THE INVENTION

Cathodic protection is a method commonly used to mitigate corrosion of buried steel structures such as pipelines; and cathodic protection systems are increasingly being used to prevent corrosion of steel reinforcement (rebar) in concrete structures. A standard criterion typically used to establish whether cathodic protection is achieved in any particular system is the −0.85 Volt Cu/CuSO$_4$ criterion. NACE Recommended Practice RP-01-69, "Control of External Corrosion on Underground or Submerged Metallic Piping Systems." If the potential of the structure is −0.85 Volt or more negative, with respect to a Cu/CuSO$_4$ reference electrode, oxidation reactions which produce corrosion should not occur and the protected structure should not corrode. Id.

There are several deficiences with an absolute criterion. Potential measurements are affected by a voltage (IR) drop in the soil or concrete media which adds a negative voltage to the potential measured. T. J. Barlo, and R. R. Fessler, *Annual Report On Project PR-3-93*, American Gas Association, Arlington, Va., Catalog No. L51394 (1979); N. G. Thompson, G. T. Ruck, K. J. Walcott, and G. H. Koch, *Annual Report on "Phase IV-Effectiveness of Cathodic Protection,"* For The Gas Research Institute (1986). The IR-drop in the media makes the measured potential more negative than the actual polarization potential. For example, if a measured potential is −0.92 Volt and a 0.10 volt IR-drop occurs, the actual polarized potential is −0.82 Volt. In this example, thus, while the measured potential appears to exceed −0.85 Volt, the actual polarized potential of the cathodic protection systems does not meet the standard criterion. There is thus a need for a monitoring method for cathodic protection systems that can compensate for IR-drop in a soil or concrete media.

Furthermore, potential measurements do not provide a direct measure of corrosion. The −0.85 V criterion is empirical and does not apply to all soil or concrete conditions. For example, for low moisture content soil conditions, potentials more positive than −0.85 Volt can provide sufficient cathodic protection to mitigate corrosion. T. J. Barlo, N. G. Thompson, A. J. Markworth, J. H. Holbrook, and W. E. Berry, *Final Report on PR-3-129 : An Assessment Of The Criteria For Cathodic Protection Of Buried Pipelines*, American Gas Association, Arlington, Va. (1983). In such circumstances where the −0.85 Volt criteria is arbitrarily used, cathodic "over protection" may result. On the other hand, where biologically induced corrosion occurs or where sulfides are present, −0.85 Volt may not be an adequate cathodic protection level. It is, thus desirable to provide a monitoring technique which can directly detect corrosion and establish whether an applied level of cathodic protection is sufficient.

Electrochemical impedance spectroscopy has been used to study the corrosion of steel in soil, J. N. Murray, J. R. Scully, and P. J. Moran, *Proceedings of NACE Corrosion/86*, Paper No. 271, Houston, Tex. (1986), and concrete. J. L. Dawson, J. A. Richardson, L. M. Callow, and K. Hladky, *Proceedings of NACE corrosion/78*, Paper No. 125, Houston, Tex. (1978); D. G. John, P. C. Searson, and J. L. Dawson, *British Corrosion Journal*, 16, 2, p. 102 (1981). Electrochemical impedance spectroscopy has also been used to study cathodically protected condenser tubes. M. C. H. Mckubre, *EPRI Report No. C5-2858*, Research Project 1689-7 (1983). Theoretical analysis showed the possibility of estimating corrosion rates for metals under cathodic protection. Several considerations, however, make the practical application of electrochemical impedance spectroscopy analysis difficult in cathodic protection systems in soil and concrete. These include the unknown native free-corrosion potential prior to application cathodic protection, the unknown polarized potential due to IR-drop in the media, and a change in local environment resulting from the applied cathodic protection current that alters the electrode kinetics.

Electrochemical impedance spectroscopy studies have also been performed for carbon steel in soils for both freely corroding and cathodically polarized conditions. N. G. Thompson, G. T. Ruck, K. J. Walcott, and G. H. Koch, *Annual Report on "Phase IV-Effectiveness of Cathodic Protection"* For The Gas Research Institute (1986); G. T. Ruck, K. J. Walcott, N. G. Thompson, and T. J. Barlo, *Annual Report On Phase III-Effectiveness of Cathodic Protection*, The Gas Research Institute, Chicago, Ill., November, 1985; and N. G. Thompson, K. J. Walcott, G. T. Ruck, and K. B. Burnham, "Instruments To Monitor The Level Of Cathodic Protection On Buried Pipelines," *Proceedings Of The 1986 International Gas Research Conference*, Toronto, Canada, September, 1986. The studies appear to establish a basic spectral difference between the corroding conditions and cathodically polarized conditions in soil when the cathodic protection system is subjected to electrochemical impedance spectroscopy analysis.

In the present invention, the spectral difference appearing between cathodically protected and corroding conditions when a cathodic protection system is subjected to an electrochemical impedance spectroscopy analysis provides a needed and useful means by which the presence or absence of corrosion may be detected.

BRIEF DESCRIPTION OF THE DRAWINGS

FIG. 2 shows schematics of equivalent electrical circuits for models used in which FIG. 2a represents a charge transfer control situation and FIG. 2b represents a diffusional control situation corresponding to the presence of corrosion.

DESCRIPTION OF THE PREFERRED EMBODIMENT

The preferred embodiment of the invention comprises a method for determining the presence or absence of corrosion of a cathodically protected carbon steel structure. In the method, a spectrum (i.e., a plurality) of different discrete sine wave frequencies at either a predetermined voltage or a predetermined current is superimposed over the ambient cathodic protection current or voltage applied to the structure. The system response to the superimposed voltage or current is measured in terms of the impedance change resulting from the superimposed signal. An electrochemical impedance spectrum analysis over the predetermined spectrum of frequencies superimposed is made. At predetermined frequencies, impedance of the system includes a real and imaginary component for that frequency. The real component of the impedance of the system and the imaginary component of the impedance of the system are each measured. Analysis of the frequency dependence of these values permits a determination whether corrosion is occuring.

In one analytical method, a Nyquist plot of real vs. imaginary impedance can be made over the spectrum of frequencies. From an analysis of the plot, whether corrosion is occurring can be determined by means of a matrix with respect to the shape of the plot. In a Nyquist plot, a semi-circular plot of the real vs. imaginary components of the impedance indicates that corrosion is not occuring and that the level of cathodic protection is adequate; a linear plot indicates that corrosion is occurring.

Other plotting schemes provide a comparable system of analysis.

In these analytical methods, it is the presence of a Warburg impedance in the system which indicates that corrosion exists.

Figure 1:
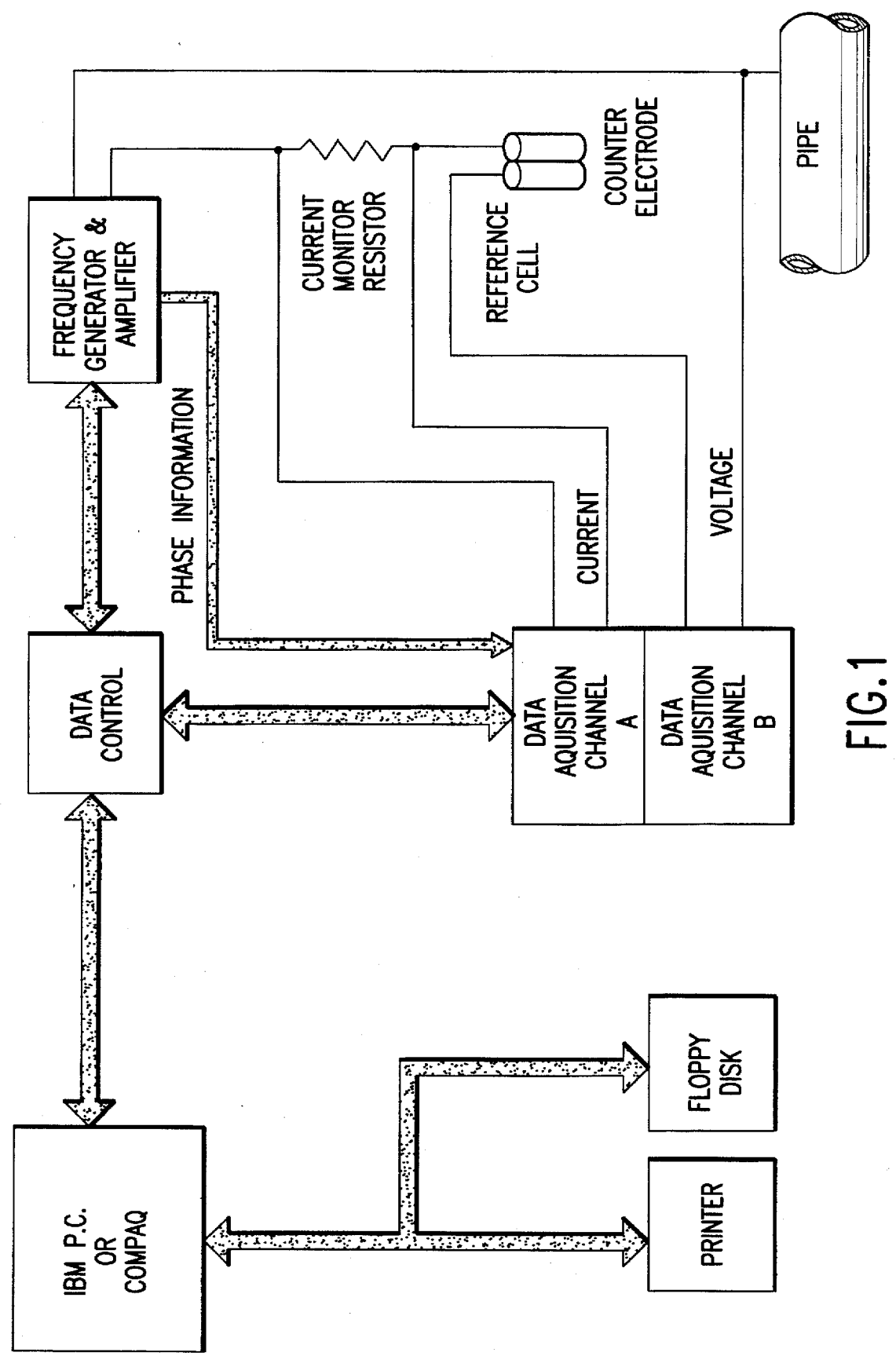
FIG. 1 is a block diagram of spectroscopy apparatus useful with the invention.

The key requirement of apparatus useful in the invention is that it can evaluate AC-impedance in the cathodic protection circuit. A block diagram of a system is shown in FIG. 1. Typically, the frequency generator and amplifier, 1, are used to apply frequencies in the range of $10^{-2}$ to $10^5$ Hz. with appropriate amplitudes and DC bias. Phase and amplitude information of signals is supplied to data acquisition Channel A, 2, and Channel B, 3. Channel A and Channel B monitor relative phase and amplitude of the current and voltage. A computer or central processing unit, 4, is used to control functions, and data can be stored on floppy disk, 5, or printed, 6, as desired. With reference to FIG. 1, the cathodically protected system, such as a pipeline, is shown at 7. The reference cell, 8, provides the voltage measurement means and the counter electrode, 9, is the means by which the electrochemical impedance spectroscopy signal is superimposed on the system. The current monitor resistor, 10, is a means for providing the current measurement. The apparative configuration is standard to those of skill in the electrochemical impedance spectroscopy art.

EXAMPLES

Electrochemical impedance spectroscopy data for test cells were obtained using a Solartron 1250 Frequency Response Analyzer (FRA) in conjunction with a Princeton Applied Research Model 273 Potentiostat/Galvanostat interfaced to an Apple IIe central processing unit which performed functions of data processing, storage and analysis. Standard electrochemical impedance spectroscopy techniques were employed.

The potentiostat provided the electrochemical interface between the FRA and the test specimen. The generated sine wave from the FRA of ±15mV was applied to the external input of the potentiostat. The electrometer output of the potentiostat and the voltage drop across a resistor in the counter electrode lead provided the potential and current input to the FRA respectively.

I.

DESCRIPTION OF SPECIMENS

Figure 3:
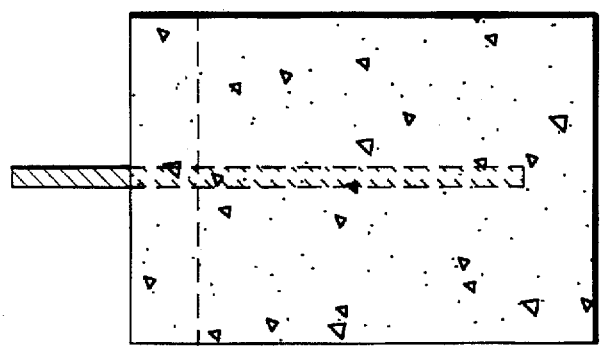
FIG. 3 shows the specimen configuration used in the Examples herein.

To establish normal and accelerated corrosion rates in concrete, carbon steel rods 6.0 inch long and 0.25 inch in diameter were first given a uniform surface finish by grinding with 60 grit silicon carbide paper. This rough finish promoted adhesion of concrete to the rod. The rods were then degreased and cast extending concentrically 4.5 inch into 2.75 inch diameter concrete cylinders 5.0 inch in height, of a commercially mixed Portland cement containing a maximum aggregate size of 0.375 inch. Eight such carbon steel specimen rods were cast in concrete prepared using a 50,000 $g/m^3$ NaCl solution with a solution-cement ratio of 1:9.3. Eight like specimens were cast in concrete prepared using a 1:9.6 ratio of tap water to concrete. FIG. 3 shows the general sample configuration.

The eight samples prepared with the NaCl solution were immersed in a 50,000 $g/m^3$ NaCl bath and the eight specimens prepared with tap water were immersed in tap water. For each solution, duplicate specimens were polarized galvanostatically to three potentials, -0.85, -1.0, and -1.2 Volt Cu/CuSO$_4$. Duplicate specimens were allowed to freely corrode. For the polarized specimens a graphite counter electrode was used. A summary of the test conditions is given in Table 1.

TABLE 1

TEST CONDITIONS FOR CONCRETE SPECIMENS.

| SAMPLE ID | CONDITION | POLARIZED POTENTIAL Cu/CuSO$_4$ | APPLIED CURRENT (mA) |
|---|---|---|---|
| C1 | 50,000 g/m$^3$ NaCl | -1.0 | -.076 |
| C2 | 50,000 g/m$^3$ NaCl | -1.0 | -.098 |
| C3 | 50,000 g/m$^3$ NaCl | -0.85 | -.02 |
| C4 | 50,000 g/m$^3$ NaCl | -0.85 | -.05 |
| C5 | 50,000 g/m$^3$ NaCl | -0.500 | — |
| C6 | 50,000 g/m$^3$ NaCl | -0.528 | — |
| C7 | 50,000 g/m$^3$ NaCl | -1.2 | -1.927 |
| C8 | 50,000 g/m$^3$ NaCl | -1.2 | -1.130 |
| C9 | Tap Water | -1.0 | -0.299 |
| C10 | Tap Water | -1.0 | -0.343 |
| C11 | Tap Water | -0.85 | -0.068 |
| C12 | Tap Water | -0.85 | -0.066 |
| C13 | Tap Water | -0.007 | — |
| C14 | Tap Water | -0.007 | — |
| C15 | Tap Water | -1.2 | -1.322 |
| C16 | Tap Water | -1.2 | -1.479 |

Samples C5, C6, C13 and C14 were maintained at free corrosion potential.

Figure 2:
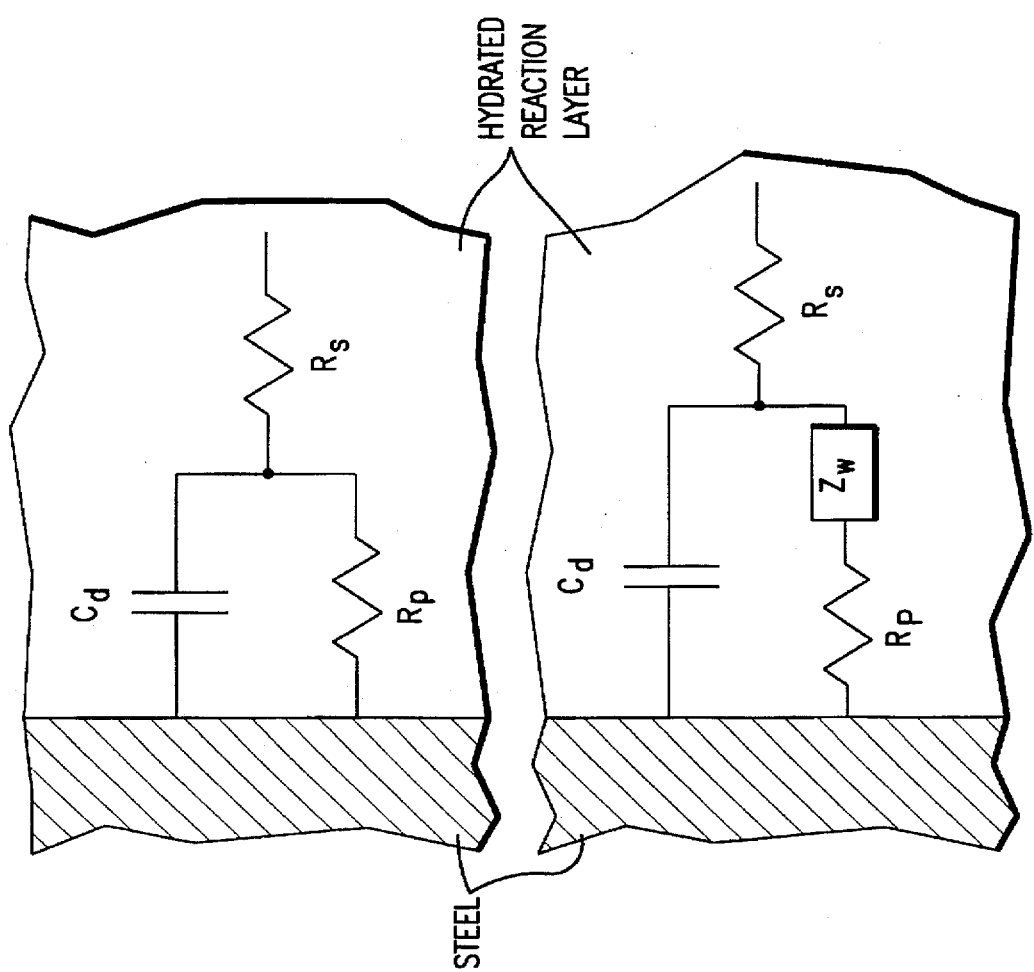

The two equivalent electrical circuits shown in FIG. 2 were used as models for the metal-solution electrochemical interface of the test specimens. The steel surface is considered to present a hydrated reaction layer which presents a corrosion site. The first equivalent circuit, FIG. 2a, models a metal-solution interface under charge transfer control, i.e., cathodically protected. In this model $R_s$ represents the solution resistance, $R_p$ represents the charged transfer resistance (polarization resistance) and $C_d$ represents the capacitance of the interface (double layer capacitance). The second model, FIG. 2b, includes a Warburg impedance, $Z_w$, which represents the impedance of a diffusion controlled process occurring at the steel surface interface, i.e., a system in which corrosion is occuring.

This model is also a fair representation of a steel surface in soil and is applicable to specimens at the free-corrosion potential when the corrosion rate of the specimen is very low (0.25 mpy or less) specimens that are cathodically polarized and the corrosion rate is low (less than 0.25 mpy) and significant pitting does not occur.

Figure 4A:
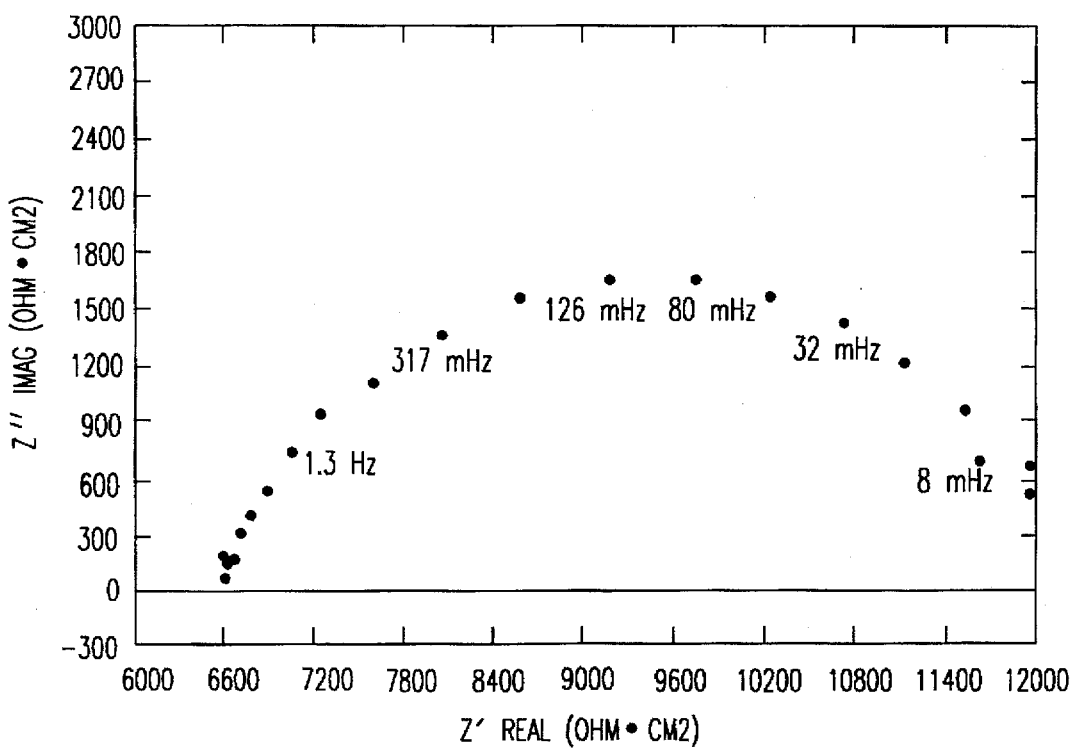
FIG. 4 shows a Nyquist plot corresponding to the absence of corrosion in a cathodically protected tap water system.
Figure 4B:
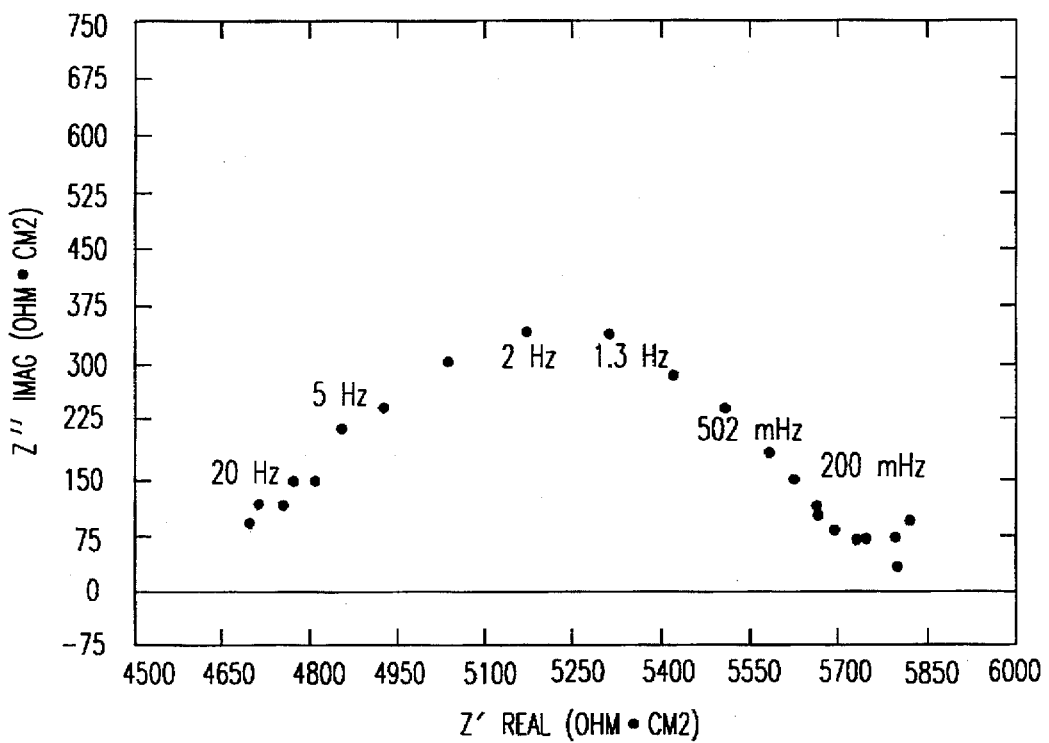

As noted above, a Nyquist plot is one means for visualizing test results. For the ideal case of the charge transfer model, indicating an appropriate level of cathodic protection, the Nyquist plot is represented by a semicircle with the high frequency intersection of the X-axis equal to $R_s$ and the low frequency intersection of the X-axis equal to $_sR_s+R_p$. This plot is shown in FIG. 4. When corrosion exists, the Warburg impedance creates a diversion from the ideal semicircular behavior of the Nyquist plot at the low end of the frequency spectrum and the ideal Warburg impedance is represented by a linear line with a slope of 1. This difference in the plot display arising from the presence of a Warburg impedance at the corroding steel surface is the criterion by which the presence of corrosion is detected in the present invention.

III.

RESULTS

Electrochemical impedance spectroscopy was performed for the carbon steel—concrete specimens identified in Table I immersed in tap water and the 50,000 g/m³ NaCl solution.

A. The Tap Water Specimens

The tap water specimens at exposure times of 72 and 744 hours exhibited a reasonably good fit to a Nyquist plot semicircle showing no signs of diffusion controlled behavior at the steel interface, implying a negligible corrosion rate. This behavior is expected for carbon steel under these conditions. Post-test examination of the carbon steel surface confirmed that negligible corrosion had occurred.

The carbon steel-concrete specimens polarized to −0.85, −1.0, and −1.2 V Cu/CuSO$_4$, respectively, indicated that the reaction sequences are under charge transfer control and were adequately modeled by FIG. 2a. FIG. 4 represents sample C10. These curves represent relatively low values of $R_p$ which, under cathodic polarization, represent the applied cathodic current and not the corrosion rate. However, the semicircles are depressed for the two more negative cathodic potentials. It has been suggested that depressed semicircles for the Nyquist plots could be caused by time constant dispersion due to inhomogeneities in the electrode surface. K. Hladky, L. M. Callow, and J. L. Dawson, *British Corrosion Journal*, 15, 1, p. 20 (1980).

B. The Salt Solution Specimens

Figure 5A:
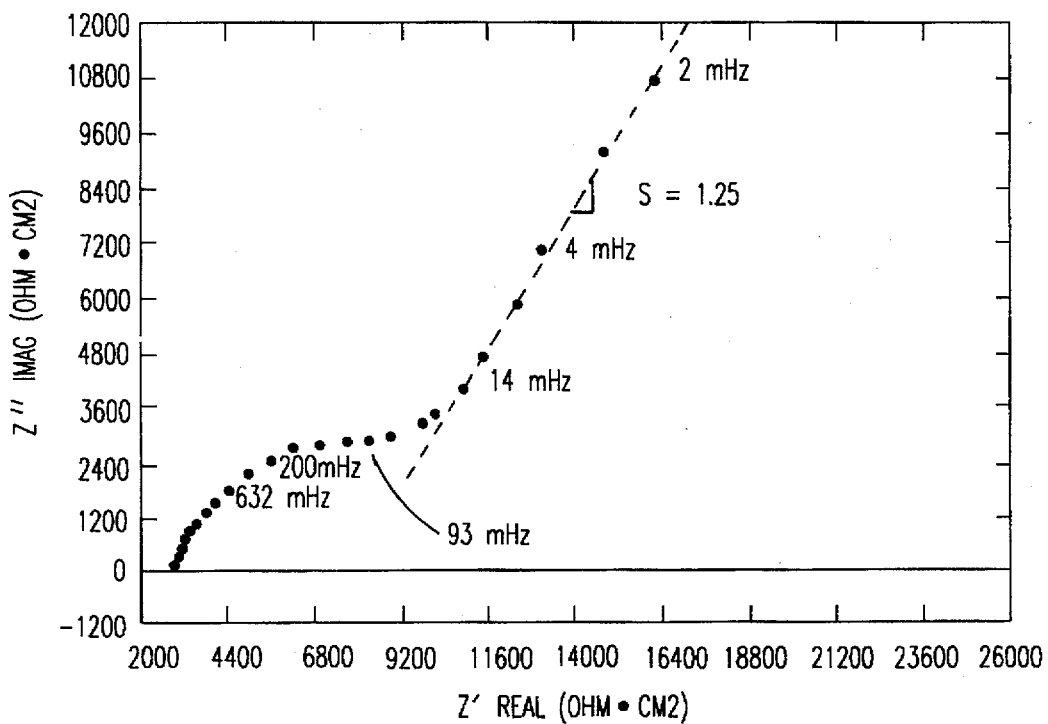
FIG. 5 shows a sample Nyquist plot for freely corroding carbon steel specimens in concrete immersed in NaCl solution.
Figure 5B:
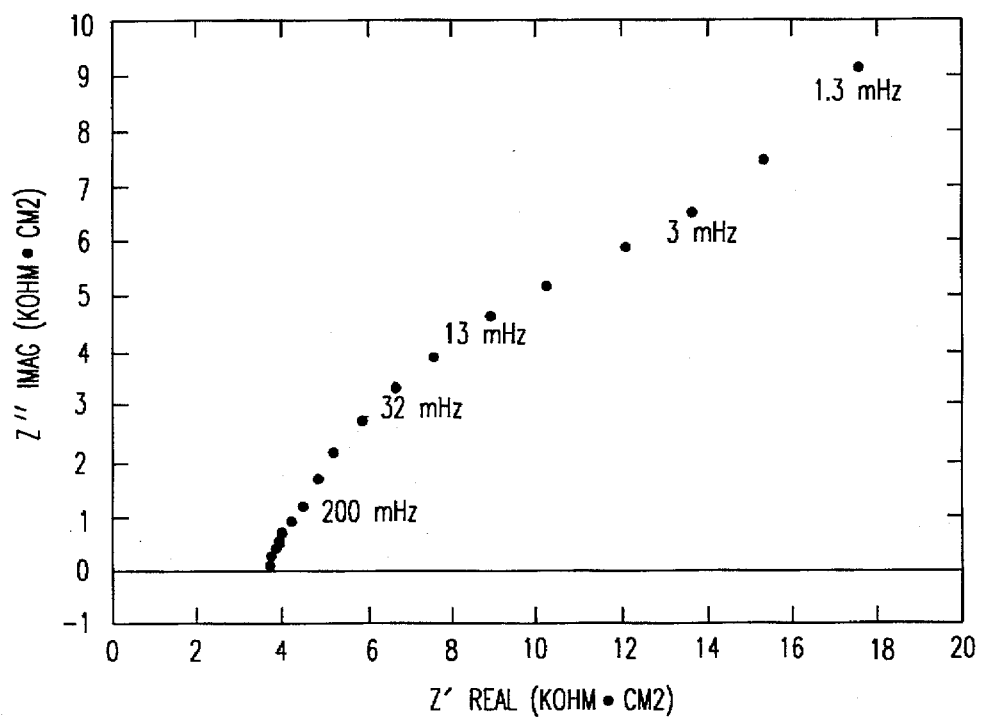
Figure 6A:
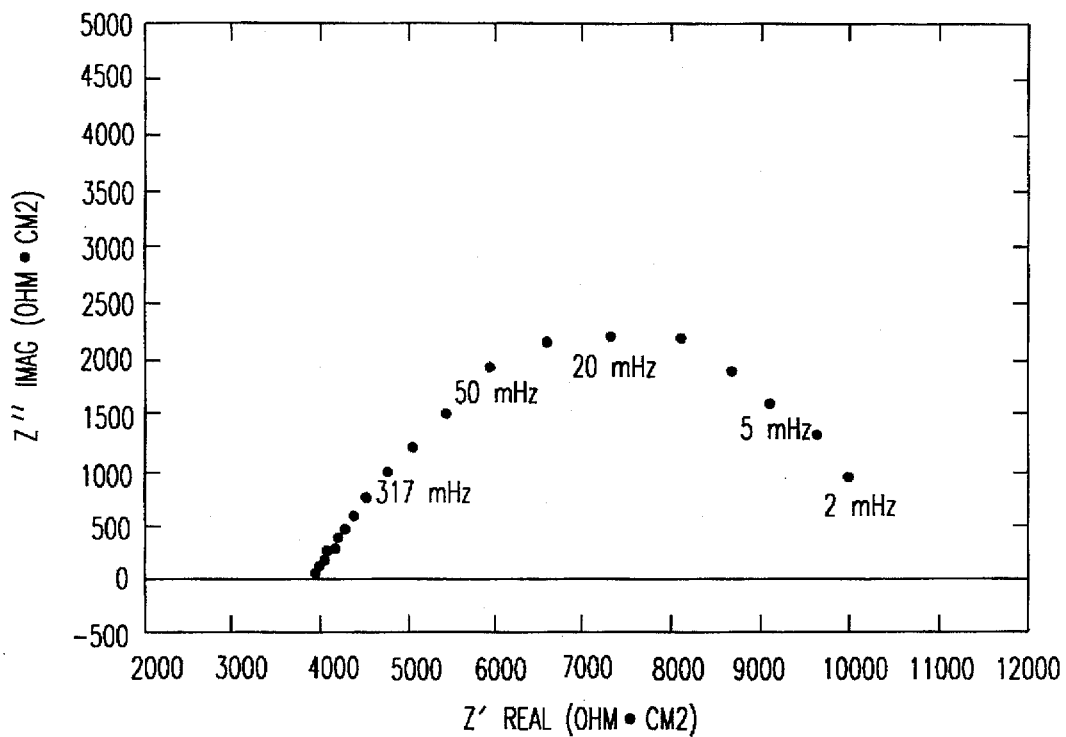
FIG. 6 shows a sample Nyquist plot for carbon steel in concrete immersed in NaCl solution and polarized to −1.2 Volt Cu/CuSO$_4$ after 816 hours exposure, indicating effective cathodic protection.
Figure 6B:
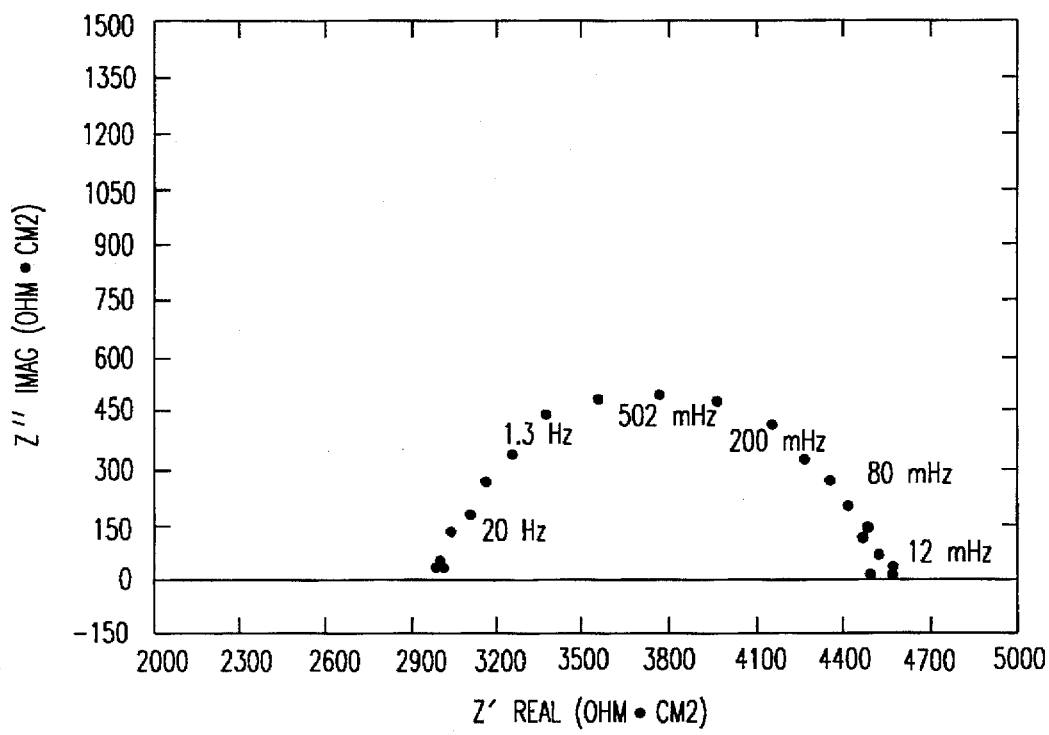

For the specimens immersed in the NaCl solution, FIGS. 5 and 6, respectively, show the Nyquist plots for two carbon steel-concrete specimens, C6 and C8, exposed to the NaCl solution. In FIG. 5 the Warburg impedance is represented by a slope of Z" versus Z' near +1 at lower frequencies which indicates a diffusion controlled process occurring at the steel surface i.e., corrosion. Specimen No. C5 showed almost entirely diffusion controlled behavior even at high frequencies and even during initial exposure. For Specimen No. C6, early stages of exposure showed more classical diffusional behavior indicating a partial charge transfer semicircle at high frequencies and a Warburg impedance of slope −1 at lower frequencies.

FIG. 6, representing specimen No. C8, shows a semicircle with no signs of diffusion control displaying a behavior similar to that observed for specimens in tap water polarized to −1.0 and −1.2 V.

ANALYSIS OF ELECTROCHEMICAL
IMPEDANCE SPECTROSCOPY DATA
FREQUENCY AT MAXIMUM PHASE SHIFT FOR EACH
SPECIMEN DURING THE LATTER STAGES OF EXPOSURE.

| SAMPLE ID | SOLUTION | POLARIZED POTENTIAL V, Cu/CuSO$_4$ | FREQUENCY AT MAX PHASE SHIFT, Hz |
|---|---|---|---|
| C1 | NaCl | −1.0 | .003 |
| C2 | NaCl | −1.0 | .05 |
| C3 | NaCl | .85 | .02 |
| C4 | NaCl | .85 | .002 |
| C5 | NaCl | FC | .002 |
| C6 | NaCl | FC | .001 |
| C7 | NaCl | −1.2 | 1.6 |
| C8 | NaCl | −1.2 | 1.0 |
| C9 | Tap Water | −1.0 | .3 |
| C10 | Tap Water | −1.0 | .8 |
| C11 | Tap Water | −.85 | .006 |
| C12 | Tap Water | −.85 | .01 |
| C13 | Tap Water | FC | .02 |
| C14 | Tap Water | FC | .02 |
| C15 | Tap Water | −1.2 | 1.6 |
| C16 | Tap Water | −1.2 | 1.6 |

The detection method of the invention utilizes the fact that significant changes occur in the electrochemical impedance spectroscopy spectra when the environment of the cathodically protected structure changes from corroding conditions to cathodically protected conditions. For soil conditions examined and for concrete with NaCl additions, the corrosion process is characterized as a diffusion controlled reaction sequence. Upon application of cathodic protection, the type of reaction sequence goes from one of diffusion control (corrosion) to charge transfer control (reduction reactions).

These results show the utility of electrochemical impedance spectroscopy as a monitoring tool for detecting corrosion on cathodically protected structures. Presently used monitoring practices involve potential measurements or current flow measurements in the environment, which provide indirect indications of corrosion. The electrochemical impedance spectroscopy method provides the corrosion engineer with a certain and direct indication of the presence of corrosion on a structure being cathodically protected.

What is claimed is:

1. A method for determining corrosion of a cathodically protected steel structure in a soil or concrete medium, said method comprising the steps of:

superimposing a plurality of discrete sine wave frequencies at a predetermined voltage over an ambient cathodic protection voltage applied to said structure;

measuring the electrochemical impedance of said structure at each of said frequencies;

determining a real and an imaginary component of said impedance at each of said frequencies;

plotting said real component of said impedance versus said imaginary component of said impedance at each of said frequencies;

determining corrosion of said structure directly from said plot independent of a calculating step, a generally linear plot indicating the presence of corrosion and a generally semi-circular plot indicating the absence of corrosion.

2. A method for determining corrosion of a cathodically protected steel structure in a soil or concrete medium, said method comprising the steps of:

superimposing a plurality of discrete sine wave frequencies at a predetermined current over an ambient cathodic protection current applied to said structure;

measuring the electrochemical impedance of said structure at each of said frequencies;

determining a real and an imaginary component of said impedance at each of said frequencies;

plotting said real component of said impedance versus said imaginary component of said impedance at each of said frequencies;

determining corrosion of said structure directly from said plot independent of a calculating step, a generally linear plot indicating the presence of corrosion and a generally semi-circular plot indicating the absence of corrosion.

* * * * *